US010444124B2

(12) United States Patent
Miyawaki et al.

(10) Patent No.: US 10,444,124 B2
(45) Date of Patent: *Oct. 15, 2019

(54) CLARIFYING REAGENT FOR BIOLOGICAL MATERIALS AND USE THEREOF

(75) Inventors: Atsushi Miyawaki, Wako (JP); Hiroshi Hama, Wako (JP); Asako Sakaue, Wako (JP)

(73) Assignee: RIKEN, Wako-shi, Saitama (JP)

(*) Notice: Subject to any disclaimer, the term of this patent is extended or adjusted under 35 U.S.C. 154(b) by 335 days.

This patent is subject to a terminal disclaimer.

(21) Appl. No.: 14/118,150

(22) PCT Filed: May 18, 2012

(86) PCT No.: PCT/JP2012/062874
§ 371 (c)(1),
(2), (4) Date: Nov. 15, 2013

(87) PCT Pub. No.: WO2012/161143
PCT Pub. Date: Nov. 29, 2012

(65) Prior Publication Data
US 2014/0178927 A1    Jun. 26, 2014

(30) Foreign Application Priority Data
May 20, 2011   (JP) ................................. 2011-114009

(51) Int. Cl.
*G01N 1/30* (2006.01)
*G01N 33/50* (2006.01)

(52) U.S. Cl.
CPC .......... *G01N 1/30* (2013.01); *G01N 33/5002* (2013.01); *G01N 33/5005* (2013.01); *G01N 33/5008* (2013.01); *G01N 2001/302* (2013.01)

(58) Field of Classification Search
CPC .. G01N 1/30; G01N 33/5002; G01N 33/5005; G01N 33/5008; G01N 2001/302
See application file for complete search history.

(56) References Cited

U.S. PATENT DOCUMENTS

| | | | |
|---|---|---|---|
| 2,029,525 A | 2/1936 | Ellis | |
| 4,493,821 A | 1/1985 | Harrison | |
| 4,578,282 A | 3/1986 | Harrison et al. | |
| 4,748,189 A | 5/1988 | Su et al. | |
| 4,981,610 A | 1/1991 | Linden et al. | |
| 5,350,687 A | 9/1994 | Odink et al. | |
| 5,530,100 A | 6/1996 | Darling et al. | |
| 5,612,028 A | 3/1997 | Sackier et al. | |
| 5,624,682 A | 4/1997 | Dondi | |
| 5,702,920 A | 12/1997 | Odink et al. | |
| 6,072,086 A | 6/2000 | James et al. | |
| 6,207,408 B1 | 3/2001 | Essenfeld et al. | |
| 6,232,092 B1 | 5/2001 | Rogers | |
| 6,319,683 B1 | 11/2001 | James et al. | |
| 6,462,071 B1 | 10/2002 | Castillejos | |
| 6,472,216 B1 | 10/2002 | Chiang | |
| 6,703,242 B1 | 3/2004 | Senatorov | |
| 6,891,023 B1 | 5/2005 | De Acosta Del Rio et al. | |
| 7,008,960 B1 | 3/2006 | Castillejos | |
| 8,383,403 B2 * | 2/2013 | Wang | G01N 33/80 435/2 |
| 2001/0000487 A1 | 4/2001 | Essenfeld et al. | |
| 2001/0031482 A1 | 10/2001 | James et al. | |
| 2001/0043884 A1 | 11/2001 | Essenfeld | |
| 2001/0051365 A1 | 12/2001 | Morales | |
| 2003/0199574 A1 | 10/2003 | Karageozian et al. | |
| 2004/0004075 A1 | 1/2004 | Morales et al. | |
| 2004/0033612 A1 | 2/2004 | Senatorov | |
| 2004/0043082 A1 | 3/2004 | Karageozian | |
| 2005/0137124 A1 | 6/2005 | Castillejos | |
| 2005/0142142 A1 | 6/2005 | Burrows et al. | |
| 2007/0105950 A1 | 5/2007 | Karageozian et al. | |
| 2007/0225727 A1 | 9/2007 | Matsuhisa | |
| 2008/0125580 A1 | 5/2008 | Pizarro et al. | |
| 2008/0153127 A1 | 6/2008 | Morales et al. | |
| 2008/0160542 A1 | 7/2008 | Yasuda et al. | |
| 2008/0280980 A1 | 11/2008 | Van Dyke | |
| 2009/0104654 A1 | 4/2009 | Kram et al. | |
| 2009/0191138 A1 | 7/2009 | Dechow | |
| 2009/0263342 A1 | 10/2009 | Glenn, Jr. | |
| 2010/0285560 A1 | 11/2010 | Wang | |
| 2011/0123979 A1 | 5/2011 | Salmon et al. | |
| 2011/0294990 A1 | 12/2011 | Pizarro et al. | |

(Continued)

FOREIGN PATENT DOCUMENTS

| | | |
|---|---|---|
| CN | 1068653 | 2/1993 |
| CN | 1337462 | 2/2002 |

(Continued)

OTHER PUBLICATIONS

Hama et al. (Sca/e: a chemical approach for fluorescence imaging and reconstruction of transport mouse brain. Nature Neuroscience 14(11): 1481-1488 with Technical Reports (Nov. 2011)).*
Chiang, Ann-Shyn, et al., "Insect NMDA receptors mediate juvenile hormone biosynthesis," PNAS, Jan. 8, 2002, vol. 99, No. 1, pp. 37-42.
Dodt, Hans-Ulrich, et al., "Ultramicroscopy: three-dimensional visualization of neuronal networks in the whole mouse brain," Nature Methods, vol. 4, No. 4, Apr. 2007, pp. 331-336.
Sakaue-Sawano, Asako, et al., "Visualizing Spatiotemporal Dynamics of Multicellular Cell-Cycle Progression," Cell, 132(3): pp. 487-498 (2008).

(Continued)

*Primary Examiner* — Gailene Gabel
(74) *Attorney, Agent, or Firm* — Casimir Jones, SC; Robert A. Goetz (57) ABSTRACT

A clearing reagent according to the present invention for making a biological material transparent is a solution containing: at a concentration of 1M or more and not more than 8.5M, at least one compound selected from the group consisting of urea and urea derivatives; and glycerol at a concentration of 25 (w/v) % or more and not more than 35 (w/v) %.

19 Claims, 5 Drawing Sheets

(56) References Cited

U.S. PATENT DOCUMENTS

| | | | |
|---|---|---|---|
| 2012/0196937 A1 | 8/2012 | Karageozian et al. | |
| 2013/0023008 A1 | 1/2013 | Becker et al. | |
| 2013/0045503 A1* | 2/2013 | Miyawaki | G01N 1/30 435/40.5 |
| 2013/0065217 A1 | 3/2013 | Mangino | |
| 2013/0123474 A1 | 5/2013 | Pizarro et al. | |
| 2013/0188038 A1 | 7/2013 | Tanimoto et al. | |
| 2014/0087419 A1* | 3/2014 | Miyawaki | G01N 1/30 435/40.5 |
| 2014/0287429 A1 | 9/2014 | Kasamatsu | |
| 2015/0346196 A1 | 12/2015 | Riken | |
| 2016/0169776 A1 | 6/2016 | Riken | |

FOREIGN PATENT DOCUMENTS

| | | | |
|---|---|---|---|
| CN | 101042317 | 9/2007 | |
| CN | 101871855 | 10/2010 | |
| CN | 101995474 A | 3/2011 | |
| CN | 101995475 A | 3/2011 | |
| EP | 0333328 | 9/1989 | |
| EP | 2133069 | 12/2009 | |
| JP | 63-157997 A | 6/1988 | |
| JP | 6-080502 | 3/1994 | |
| JP | 2003-066035 A | 3/2003 | |
| JP | 2003-514831 | 4/2003 | |
| JP | 2005-522464 | 7/2005 | |
| JP | 2007-051957 * | 3/2007 | G01N 27/62 |
| JP | 2007/070494 | 3/2007 | |
| JP | 2008-161138 | 7/2008 | |
| JP | 2008-524592 | 7/2008 | |
| JP | 2009-221252 | 10/2009 | |
| JP | 2011-012226 | 1/2011 | |
| WO | 94/00986 | 1/1994 | |
| WO | 2007/061783 | 5/2007 | |
| WO | 2008/008975 | 1/2008 | |
| WO | 2008/088403 | 7/2008 | |
| WO | 2010/007350 | 1/2010 | |
| WO | 2011/096468 A1 | 8/2011 | |
| WO | 2011/111876 | 9/2011 | |
| WO | 2012/147965 | 11/2012 | |
| WO | 2013/155064 | 10/2013 | |
| WO | 2013/191274 | 12/2013 | |
| WO | 2014/010633 | 1/2014 | |

OTHER PUBLICATIONS

English translation of Chinese Office Action, CN Patent Application No. 201280023902.6, mailed Apr. 22, 2015.
CN Office Action, CN Patent Application No. 201280023902.6, mailed Apr. 22, 2015.
European Search Report of corresponding EP Patent Application No. 12788804.8 dated Dec. 1, 2014, 4 pages.
Khoudoli, G. et al., "Optimisation of the two-dimensional gel electrophoresis protocol using the Taguchi approach", Proteome Science, Biomed Central, 2014, vol. 2, No. 1, pp. 1-12.
Office Action mailed Jun. 8, 2016 against related U.S. Appl. No. 13/583,548.
Baird et al., "Biochemistry, mutagenesis, and oligomerization of DsRed, a red fluorescent protein from coral", PNAS., vol. 97, No. 22, Oct. 24, 2000, pp. 11984-11989.
Bondos et al. (Analytical Biochemistry, vol. 316, p. 223-231, 2003).
Caetano-Anolles (1997). Ch XIII in Fingerprinting Methods based on Arbitarity Primed PCR, ISBN (online): 978-3-642-60441-6, p. 119-134.
Chinese Office Action of corresponding CN Patent Application No. 201180013354.4, dated Sep. 29, 2015, English translation included.
Clarke, Jonathan, et al., "Distribution and Neuronal Expression of Phosphatidylinositol Phosphate Kinase IIγ in the Mouse Brain," The Journal of Comparative Neurology, 517:296-312 (2009).
CN Office Action, CN Application No. 201280020354.1, mailed Mar. 3, 2015, English translation provided.

Das Gupta et al. (1989) Effects of urea and a nonionic surfactant on the micellization and counterion binding properties of cetyltrimethyl ammonium bromide and sodium dodecyl sulfate. Colloid & Polymer Science, v267, 9246-254.
EP Search Report mailed Aug. 19, 2014 for EP Patent Application No. 12777671.4.
European Search Report of corresponding EP Patent Application No. 11753531.0, dated Mar. 24, 2015.
Feng et al., "Imaging Neuronal Subsets in Transgenic Mice Expressing Multiple Spectral Variants of GFP", Neuron, vol. 28, Oct. 2000, pp. 41-51.
Hadjantonakis, Anna-Katerina, et al., "Embryonic stem cells and mice expressing different GFP variants for multiple non-invasive reporter usage within a single animal," BMC Biotechnology, 2:11, pp. 1-9, Jun. 11, 2002.
Hamnes et al. (1967). An investigation of water-urea and water-urea-polyethylene glycol interactions. JACS, v89(2), 9442-446.
Honma, "A Study of the Vascular Network of Sciatic Nerves in Experimental Chronic Diabetic Rat", Journal of St. Marianna University School of Medicine Hospital, vol. 27, No. 4, Aug. 1, 1999, pp. 339-347.
Hurkman et al. (1986). Solubilization of plant membrane proteins for analysis by two-dimensional gel electrophoresis. Plant Physiology, v81, p. 802-806.
International Search Report mailed Jun. 21, 2011, International Patent Application No. PCT/JP2011/056502.
Jansen et al. The Journal of Comparative Neurology, vol. 517, p. 296-312, 2009.
Karasawa, Satoshi, et al., "A Green-emitting Fluorescent Protein from Galaxeidae Coral and its Monomeric Version for Use in Fluorescent Labeling," The Journal of Biological Chemistry, 278(36), pp. 34167-34171 (2003).
Kyuma, "Histochemical Studies on Glycoconjugates in the Salivary Gland Connective Tissues of Laboratory Animals", Journal of Nagoya City University Medical School, vol. 42, No. 2, May 1, 1991, pp. 183-208.
McCormick et al. (Proceedings of the National Academy of Sciences, vol. 97, No. 2, p. 668-697, 2000.
Nagai, Takeharu, et al., "A variant of yellow fluorescent protein with fast and efficient maturation for cell-biological applications," Nature Biotechnology, vol. 20, Jan. 2002, pp. 87-90.
Office Action dated Apr. 28, 2014, China Patent Application No. 201180013354.4, English Translation provided.
Office Action of corresponding JP Patent Application No. 2012-556745, mailed Mar. 31, 2015, English translation provided.
Sakagami et al., "Effects of treatment with urea upon the electron microscopic histochemical reactions of acidic glycoconjugates in fixed tissues", Connect Tissue, vol. 21, No. 2, Nov. 1989, pp. 37-38.
Scherer, William F., "Studies on the Propagation in Vitro of Poliomyelitis Viruses," J. Exp. Med. 97(5), pp. 695-710, May 1, 1953.
Seabold et al., Journal of Visualized Experiments, vol. 41, p. 2081-2085, 2010.
Shaw and Chambers (1721). "A New Method of Chemistry . . . ", p. 193.
Shi et al. (Journal of Histochemistry & Cytochemistry, vol. 41, p. 1599-1604, 1993).
Zhang, Guohong, et al., "An Enhanced Green Fluorescent Protein Allows Sensitive Detection of Gene Transfer in Mammalian Cells," Biochemical and Biophysical Research Communications, 227, pp. 707-711 (1996).
Office Action mailed Nov. 4, 2015, Corresponding U.S. Appl. No. 14/113,639.
Final Office Action mailed May 9, 2016, Corresponding U.S. Appl. No. 14/113,639.
Office Action mailed May 27, 2014, Corresponding U.S. Appl. No. 13/583,548.
Office Action mailed Aug. 27, 2015, Corresponding U.S. Appl. No. 13/583,548.
Final Office Action mailed Jan. 13, 2014, Corresponding U.S. Appl. No. 13/583,548.
Office Action mailed Jun. 26, 2013, Corresponding U.S. Appl. No. 13/583,548.

(56) References Cited

OTHER PUBLICATIONS

Office Action dated Jan. 23, 2017 against related U.S. Appl. No. 14/113,639.
EP Office Action, EP Application No. 12788804.8, dated Feb. 17, 2017.
Office Action dated Mar. 29, 2017 against related U.S. Appl. No. 13/583,548.
U.S. Office Action for U.S. Appl. No. 14/113,639, dated Jul. 11, 2017.
Crapo et al. An overview of tissue and whole organ decellularization processes. Biomaterials (epub Feb. 5, 2011), v32, p. 3233-3243.
Advisory Action for U.S. Appl. No. 14/113,639, dated Nov. 16, 2017.
U.S. Office Action for U.S. Appl. No. 13/583,548, dated Aug. 17, 2017.
Non-Final Office Action, U.S. Appl. No. 14/113,639, dated May 29, 2018.
Ke, Meng-Tsen et al. "SeeDB: a simple and morphology-preserving optical clearing agent for neuronal circuit reconstruction" advance online publication (published online Jun. 23, 2013).
U.S. Office Action, U.S. Appl. No. 13/583,548, dated Jun. 25, 2018.
Final Office Action, U.S. Appl. No. 14/113,639, dated Jan. 29, 2019.
Final Office Action, U.S. Appl. No. 13/583,548, dated Feb. 8, 2019.
English translation of International Preliminary report on patentability of PCT/JP2014/070618, dated Feb. 16, 2016.
Chung, Kwanghun et al. "Structural and molecular interrogation of intact biological systems" Nature vol. 497: 332-339 (2013).
Ke, Meng-Tsen et al. "SeeDB: a simple and morphology-preserving optical clearing agent for neuronal circuit reconstruction" advance online publication (published onlne Jun. 23, 2013).
Keller, Philipp J. et al. "Reconstruction of Zebrafish Early Embryonic Development by Scanned Light Sheet Microscopy" Science vol. 322: 1065-1069 (2008).
Becker, Klaus et al. "Chemical Clearing and Dehydration of GFP Expressing Mouse Brains" PLoS ONE vol. 7 issue 3: e33916 (2012).
Office Action for EP Patent Application No. 12788804.8, dated Feb. 17, 2017, 5 pages.
European Search Report, EP Patent APplication No. 14836073.8, dated Mar. 23, 2017.
Susaki et al.: Whole-brain imaging with single-cell resolution using chemical cocktails and computational analysis. Cell 157(3), 726-39 (2014).
Tainaka et al. "Whole-body imaging with single-cell resolution by tissue decolorization" Cell 159, 911-924, Nov. 6, 2014.
Chen et al. "Hoxb5 marks long-term hematopoietic stem cells and reveals a homogenous perivascular niche" Nature vol. 530 Feb. 11, 2016.
U.S. Office Action, U.S. Appl. No. 15/544,743, dated Jan. 2, 2019.
Ueda, M. et al: "Effect of sorbitol and inositol. . .", Colloid & Polymer Science, vol. 257, No. 9, Sep. 1979 (Sep. 1979), pp. 973-976, XP055508244, ISSN: 0303-402X, DOIL 10.1007/bf01520723.
Tiwari A et al: "Stabilization of yeast. . .", Biophysical Chemistry, Elsevier, Msterdam, NL, vol. 124, No. 2, Nov. 20, 2006 (Nov. 20, 2006), pp. 90-99, XP027879403, ISSN: 0301-4622.
EP Search Report, EP Patent Application No. 16740221.3, dated Sep. 27, 2018, 5 pages.
U.S. Office Action, U.S. Appl. No. 13/583,548, dated Jun. 24, 2019.
U.S. Office Action, U.S. Appl. No. 15/544,743, dated Jun. 27, 2019.
Hama, H et al. Nature Neuroscience. 2015. 18(10): 1518-1529. Supplemental Information further included. Published online Sep. 14, 2015. (Year: 2015).
CN Office Action CN Patent Application No. 201710516155.4, dated Aug. 5, 2019.
Office Action for CN Patent Application No. 201680007269.X, dated Jul. 29, 2019.
"Experimental Research on Improving Skin Light Transparency by Chemically Enhancing Permeation", Zhenzhen Han, China Excellent Master's Thesis Full-text Database, Medicine and Health Science and Technology, No. S2, pp. 4-5, 7, 12-15, 25 and 27, Dec. 2011.

* cited by examiner

CLARIFYING REAGENT FOR BIOLOGICAL MATERIALS AND USE THEREOF

CROSS REFERENCE TO RELATED APPLICATIONS

The present application is a U.S. 371 National Stage Entry of pending International Patent Application No. PCT/JP2012/062874, international filing date May 18, 2012, which claims priority to JP Patent Application No. 2011-114009, filed May 20, 2011, the contents of which are incorporated by reference in their entireties.

TECHNICAL FIELD

The present invention relates to a clearing reagent for making a biological material transparent, and use thereof.

BACKGROUND ART

For an internal observation of a non-transparent tissue with use of an optical microscope, a pretreatment (a clearing treatment for making a subject transparent) using a clearing reagent is performed.

As typical examples of the clearing reagent and the pretreatment method, there have been known (i) a Focus Clear (product name) solution described by Ann-Shyn Chiang in Patent Literature 1 and Non-Patent Literature 1 and (ii) a tissue clearing method described by Hans-Ulrich Dodt et al. in Non-Patent Literature 2. These are both used to make a tissue transparent for an observation of a fluorescent substance existing in the tissue.

CITATION LIST

Patent Literature

Patent Literature 1
U.S. Pat. No. 6,472,216 (Date of patent: Oct. 29, 2002)

Non-Patent Literatures

Non-Patent Literature 1
Ann-Shyn Chiang et al.: Insect NMDA receptors mediate juvenile hormone biosynthesis. PNAS 99(1), 37-42 (2002).
Non-Patent Literature 2
Hans-Ulrich Dodt et al.: Ultramicroscopy: three-dimensional visualization of neuronal networks in the whole mouse brain. Nature Methods 4 (4), 331-336 (2007).

SUMMARY OF INVENTION

Technical Problem

In the above-described methods, an organic solvent is essential as an active component or the like for the clearing treatment. Accordingly, the methods are hardly applicable to living tissues, and applicable to fixed samples mainly. The methods also have such a risk causing shrinkage of a biological material when the biological material is subjected to the clearing treatment.

Prior to making the present invention, the inventors of the present invention had found that it was possible to make a biological material transparent by using urea. Since urea is a component having a high bio-affinity, use of urea or a urea derivative as an active component for a clearing treatment is likely to solve the above problems.

The present inventors further made an attempt to achieve an object of developing, with use of urea or a urea derivative, a method for a clearing treatment which allows further reduction in the risk of tissue deformation even for fragile tissues.

The present invention was made in order to solve the foregoing problems, and an object of the present invention is to provide: a novel clearing agent for making a biological material transparent which clearing agent contains, as an active component, urea or a urea derivative; and use thereof.

Solution to Problem

In order to solve the foregoing problems, the present inventors made diligent studies to reach a finding that, in a case where a solution containing, as an active component for a clearing treatment, urea or a urea derivative contains glycerol at a predetermined concentration or more, it becomes possible to more reliably prevent even a fragile tissue from having tissue deformation or the like. Based on this, the present inventors arrived at the present invention.

Specifically, in order to attain the object, a clearing reagent for making a biological material transparent according to the present invention includes: at least one compound selected from the group consisting of urea and urea derivatives at a concentration of 1M or more and not more than 8.5M; and glycerol at a concentration of 25 (w/v) % or more and not more than 35 (w/v) %, the clearing reagent being a solution.

In the clearing reagent for making a biological material transparent according to the present invention, having the above arrangement, urea is contained as the compound.

The clearing reagent for making a biological material transparent according to the present invention, having the above arrangement, is an aqueous solution.

The clearing reagent for making a biological material transparent according to the present invention, having any of the above arrangements, includes a surfactant.

In the clearing reagent for making a biological material transparent according to the present invention, the surfactant is a nonionic surfactant.

In the clearing reagent for making a biological material transparent according to the present invention, the nonionic surfactant is at least one selected from the group consisting of Triton X (Registered Trademark), Tween (Registered Trademark), and NP-40 (product name).

The clearing reagent for making a biological material transparent according to the present invention, having any of the above arrangements, includes a water-soluble macromolecular compound.

In the clearing reagent for making a biological material transparent according to the present invention, the water-soluble macromolecular compound is at least one selected from the group consisting of Percoll (Registered Trademark), Ficoll (Registered Trademark), polyethylene glycol, and polyvinyl pyrrolidone.

In the clearing reagent for making a biological material transparent according to the present invention, having any of the above arrangements, the glycerol is contained at a concentration of 27 (w/v) % or more and not more than 33 (w/v) %.

In the clearing reagent for making a biological material transparent according to the present invention, having any of the above arrangements, the urea is contained at a concentration of 3M or more and not more than 5M, and the surfactant is contained at a concentration of 0.025 (w/v) % or more and not more than 5 (w/v) %.

The clearing reagent for making a biological material transparent according to the present invention, having any of the above arrangements, makes transparent (i) a tissue or an organ derived from a multicellular animal or (ii) a multicellular animal which is not a human.

In order to attain the object, a system for a clearing treatment for making a biological material transparent according to the present invention includes: any of the above clearing reagents; and the a biological material which has been isolated, the clearing reagent having permeated into the biological material in order to make the biological material transparent.

In order to attain the object, a method according to the present invention for making a biological material transparent includes the step of: causing any of the above clearing reagents to permeate into a biological material which has been isolated, in order that the biological material is made transparent.

A kit for a clearing treatment for making a biological material transparent according to the present invention includes any of the above clearing reagents.

Advantageous Effects of Invention

The present invention provides: a clearing reagent for making a biological material transparent which clearing reagent contains, as an active component, urea or a urea derivative and makes it possible to more reliably prevent tissue deformation or the like caused by a clearing treatment; and use thereof.

BRIEF DESCRIPTION OF DRAWINGS

FIG. 4A is a view in which embryos incubated with shaking at room temperature for seven days in the respective solutions are compared with each other. FIG. 4B is a graph in which a degree to which an embryo swelled is quantified.

DESCRIPTION OF EMBODIMENTS

The following will describe an embodiment of the present invention in detail.

(Active Component of Clearing Reagent for Making Biological Material Transparent)

A "clearing reagent for making a biological material transparent" according to the present invention is a solution containing "urea" as an essential active component for making a biological material transparent.

A "clearing reagent for making a biological material transparent" according to another aspect of the present invention is a solution containing a "urea derivative" as an essential active component for making a biological material transparent.

The urea derivative is not limited to any specific kind. Concretely, for example, the urea derivative is any of various kinds of ureine or compounds expressed by Formula (1) below. Note that the compounds expressed by Formula (1) include part of ureines. The clearing agent for making a biological material transparent according to the present invention only needs to contain, as an active component, at least one compound selected from the group consisting of urea and urea derivatives. Among these, the clearing agent more preferably contains urea.

[Chem. 1]

(1)

In a urea derivative expressed by Formula (1), each of R1, R2, R3, and R4 is independently a hydrogen atom (note that the one in which all of R1 through R4 are hydrogen atoms is excluded, since it corresponds to urea), a halogen atom, or a hydrocarbon group. Further, in a case where the hydrocarbon group has a plurality of carbon atoms, part of the carbon atoms may be replaced by a hetero atom such as a nitrogen atom, an oxygen atom, or a sulfur atom. Examples of the hydrocarbon group encompass a chain hydrocarbon group and a cyclic hydrocarbon group.

Examples of the chain hydrocarbon group encompass a chain alkyl group, a chain alkenyl group, and a chain alkynyl group. The chain hydrocarbon group may have any number of carbon atoms. For example, the chain hydrocarbon group may be straight-chain or branched one having 6 or less carbon atoms, preferably, an alkyl group having 1 through 3 carbon atoms. The chain hydrocarbon group may have a substituent such as a halogen atom. Examples of the chain alkyl group encompass a methyl group, an ethyl group, a propyl group, an isopropyl group, a butyl group, an iso-butyl group, a sec-butyl group, a tert-butyl group, a hexyl group, and an octyl group.

The cyclic hydrocarbon group may be, for example, a cycloalkyl group or a cycloalkenyl group. The cyclic hydrocarbon group may have a substituent such as a halogen atom. Examples of the cycloalkyl group encompass those having 3 or more and preferably not more than 6 carbon atoms, such as a cyclopropyl group, a cyclobutyl group, a cyclopenthyl group, and a cyclohexyl group. Examples of the cycloalkenyl group encompass those having 3 or more and preferably not more than 6 carbon atoms, such as a cyclohexenyl group.

Examples of the halogen atom encompass a fluorine atom, a chlorine atom, a bromine atom, and an iodine atom.

The following 1) and 2) are more preferable, concrete examples of the urea derivatives expressed by Formula 1:
1) Any three groups selected from R1 through R4 are hydrogen atoms, and the other one group is (i) a halogen atom or (ii) a chain hydrocarbon group having 1 through 6 carbon atoms, more preferably, the other one group is an alkyl group having (i) 1 through 3 carbon atoms or (ii) 1 or 2 carbon atoms.
2) Any two groups selected from R1 through R4 are hydrogen atoms, and each of the other two groups is independently (i) a halogen atom or (ii) a chain hydrocarbon group having 1 through 6 carbon atoms, more preferably, both of the other two groups are alkyl groups each having (i) 1 through 3 carbon atoms or (ii) 1 or 2 carbon atoms. Further more preferably, one of the two groups which are hydrogen atoms is selected from R1 and R2, and the other of the two groups is selected from R3 and R4.

The "clearing reagent for making a biological material transparent" according to the present invention contains at least one compound selected from the group consisting of urea and urea derivatives at a concentration of 1M or more and not more than 8.5M. Preferably, the compound is contained at a concentration of 3M or more and not more than 5M, more preferably 3.5M or more and not more than 4.5M, further more preferably 3.7M or more and not more than 4.3M.

(Advantages of Use of Urea and/or the Like as Active Component)

Urea is an extremely low toxic substance derived from a living organism. Therefore, a "clearing reagent for making a biological material transparent" according to the present invention has the following advantages: 1) The clearing reagent of the present invention can be used to make transparent not only fixed biological materials but also non-fixed (living) biological materials. 2) Urea has a relatively low possibility of damaging fluorescent proteins and quenching of fluorescence therefrom, and therefore the clearing reagent of the present invention is also applicable to an observation of a biological material with use of a fluorescent protein. 3) Urea is quite low in cost and easily available, and furthermore is easy to handle; therefore, use of the clearing reagent of the present invention allows a clearing treatment to be performed at an extremely low cost and by a simple procedure.

In addition to these advantages, the clearing reagent according to the present invention also has the following advantages: 4) Compared with conventional clearing reagents for making a biological material transparent, the clearing reagent of the present invention can greatly improve transparency of non-transparent biological materials having high light scattering properties, thereby enabling an observation of various fluorescent proteins and fluorescent substances existing in ultra-deep tissues. 5) Particularly, for brain tissues, use of the clearing reagent of the present invention makes it possible to make transparent a white matter layer, which has been a barrier against an observation of a deep portion, thereby enabling an observation of a region (e.g., corpus callosum) located deeper than the white matter layer. 6) A clearing treatment using the clearing reagent of the present invention is reversible. Specifically, merely by immersing in an equilibrium salt solution a biological material having been subjected to the clearing treatment, it is possible to bring the biological material back to a state that the biological material had before the clearing treatment. Further, before and after the clearing treatment, antigenicity of a protein and/or the like is unchanged and maintained. This allows an assay by means of a general tissue staining or immunostaining.

Note that using, instead of urea, the above-described urea derivative can provide the similar effects.

(Glycerol)

A "clearing reagent for making a biological material transparent" according to the present invention contains "glycerol" as an essential component. The "clearing reagent for making a biological material transparent" contains the glycerol at a concentration of 25 (w/v) % or more and not more than 35 (w/v) %. In general, the glycerol is used as a drying inhibition component, and in that case, the glycerol exhibits sufficient effects at a concentration of not more than 20 (w/v) %. However, in a case where the "clearing reagent for making a biological material transparent" contains the glycerol at a concentration of 25 (w/v) % or more, it is possible to more reliably prevent deformation and the like of a biological material to be subjected to the clearing treatment. As a result, even in a case where the biological material is an extremely fragile tissue, the clearing treatment can be carried out while preventing damage and deformation of the biological material. Further, in order to promptly carry out the clearing treatment, the glycerol is contained at a concentration of not more than 35 (w/v) %. Preferably, the glycerol is contained at a concentration of 25 (w/v) % or more and not more than 33 (w/v) %, more preferably 27 (w/v) % or more and not more than 33 (w/v) %. In a case where the glycerol is contained at the above-mentioned concentrations, the "clearing reagent for making a biological material transparent" according to the present invention contains at least one compound selected from the group consisting of urea and urea derivatives at a concentration of preferably 3M or more and not more than 5M, more preferably 3.5M or more and not more than 4.5M, further more preferably 3.7M or more and not more than 4.3M. In particular, in a case where a concentration of glycerol and a concentration of urea and the like are both within the ranges described above, a high speed of the clearing treatment and an effect of preventing deformation of the biological material are both achieved.

Glycerol is relatively unlikely rejected by an immune response. Further, glycerol is relatively unlikely to be accumulated in a liver, a kidney, and the like because the glycerol is unlikely to be trapped by a reticuloendothelial system. Accordingly, the "clearing reagent for making a biological material transparent" is easily applied to a living organism as a biological material. Further, the glycerol has an advantage of being relatively low in cost.

(Surfactant)

A "clearing reagent for making a biological material transparent" according to the present invention may contain a surfactant, if necessary. The surfactant is preferably a nonionic surfactant, since the nonionic surfactant gently facilitates intrusion of the present clearing reagent into a biological tissue. Examples of the nonionic surfactant encompass: fatty acid surfactants such as polyoxyethylene sorbitan monolaurate, polyoxyethylene sorbitan monopalmitate, polyoxyethylene sorbitan monostearate, and polyoxyethylene sorbitan monooleate; higher alcohol surfactants such as polyvinyl alcohol; and alkylphenol surfactants such as polyoxyethylene octylphenyl ether. Specifically, for example, the surfactant may be at least one selected from the group consisting of: Triton X (Registered Trademark) series such as Triton X-100 and Triton X-140; Tween (Registered Trademark) series such as Tween-20, Tween-40, Tween-60, and Tween-80; and NP-40 (product name). As the surfactant, a mixture of two or more kinds may be used, if necessary.

These surfactants can enhance permeability of urea with respect to a biological material, thereby improving efficiency of the clearing treatment. In particular, in a clearing treatment on a biological material (e.g., a white matter layer of brain tissues) on which a clearing treatment is relatively difficult, the clearing reagent preferably contains a surfactant.

Note that, as with the case of urea, above surfactants can enhance permeability of the urea derivative with respect to a biological material.

(Water-Soluble Macromolecular Compound)

A "clearing reagent for making a biological material transparent" according to the present invention may further contain a water-soluble macromolecular compound, if necessary. Here, the macromolecular compound refers to the one which has a molecular weight of approximately 50,000 to 60,000, for example, and which substantially never intrudes into cells. Further, the macromolecular compound is preferably the one which does not cause denaturation or the like of a biological material. Specific examples of the water-soluble macromolecular compound encompass a crosslinked sucrose macromolecular substance, polyethylene glycol, polyvinyl pyrrolidone, and Percoll (product name; a macromolecular substance obtained by covering colloidal silica with a polyvinyl pyrrolidone film). Specific examples of the crosslinked sucrose macromolecular substance encompass a macromolecular substance which is obtained by crosslinking (copolymerizing) sucrose with epichlorohydrin and which has a weight-average molecular weight of approximately 70,000, such as Ficoll PM70 (product name).

Unlike urea and a urea derivative, these water-soluble macromolecular compounds do not intrude into cells. Furthermore, these water-soluble macromolecular compounds are soluble in water. Therefore, these water-soluble macromolecular compounds are considered to contribute to controlling of an osmotic pressure difference between the inside and outside of a cell. As such, each of these water-soluble macromolecular compounds helps a biological material to be subjected to a clearing treatment maintain its original shape, and particularly contributes to prevention of swelling of the biological material. In a case where the clearing reagent according to the present invention has a relatively high osmotic pressure, the clearing reagent preferably contains any of these water-soluble macromolecular compounds. However, the present invention is not limited to this.

(Other Components)

A "clearing reagent for making a biological material transparent" according to the present invention can contain a "drying inhibition component", which is at least one compound selected from carboxy vinyl polymer, hydroxypropyl methylcellulose, propylene glycol, and macrogol, if necessary. The drying inhibition component prevents drying of a biological material subjected to a clearing treatment. In particular, in a case where the biological material after the cleaning treatment may be kept waited for a long time period before an optical microscopic observation thereof, or in a case where an optical microscopic observation of the biological material is time-consuming, the clearing reagent of the present invention preferably contains any of the above drying inhibition components. Note that glycerol, which is contained as an essential component in the "clearing reagent for making a biological material transparent" of the present invention, has a drying inhibition effect. Accordingly, the clearing reagent for making a biological material transparent has the drying inhibition effect to a reasonable extent without separately containing the drying inhibition component.

Further, in addition to the above-described "urea and/or a urea derivative", "surfactant", and "water-soluble macromolecular compound", a "clearing reagent for making a biological material transparent" according to the present invention may contain an additive(s) such as a pH adjusting agent and/or an osmotic pressure controlling agent, if necessary.

(Solvent)

A "clearing reagent for making a biological material transparent" according to the present invention is a solution containing a solvent in which urea is soluble. The solvent is not limited to any specific kind, as long as urea is soluble in the solvent. Preferably, water is used as a main solvent; particularly preferably, only water is used as the solvent. Note that, in the present invention, what is meant by the expression "water is used as a main solvent" is that a volumetric percentage of water to all solvents used is larger than that of any other solvent, and preferably that water is used in an amount which accounts for more than 50% and not more than 100% of a total volume of all solvents used. A "clearing reagent for making a biological material transparent" prepared by using water as a main solvent is referred to as a "clearing reagent for making a biological material transparent" as an aqueous solution.

In the case where water is used as a main solvent, the water may be mixed with dimethyl sulfoxide (DMSO) for application to a fixed sample, for example. It is expected that, for example, use of a mixture of DMSO and water to a fixed sample provides effects such as (i) improvement in permeability of the clearing reagent with respect to a biological material and (ii) facilitation of a clearing treatment with respect to a tissue having a keratin surface.

Main advantages of the use of water as the solvent are as follows: 1) Urea, which is an active component of a "clearing reagent for making a biological material transparent" according to the present invention, is excellent in resolvability in water; therefore, the use of water as the solvent makes it possible to prepare easily and at a low cost the clearing reagent for making a biological material transparent. 2) Compared with a case where an organic solvent is used as a main solvent, the use of water as the solvent does not involve dehydration of a biological material when the biological material is subjected to a clearing treatment; therefore, the use of water as the solvent can prevent the problem of shrinkage of a biological material. 3) Compared with a case where an organic solvent is used as a main solvent, the use of water as the solvent significantly reduces the possibility of damaging a fluorescent protein; this makes it possible to observe, with use of a fluorescent protein, a biological material having been subjected to a clearing treatment. 4) The use of water as the solvent makes it possible to apply the clearing reagent of the present invention not only to a clearing treatment on a fixed material but also to a clearing treatment on a living material. 5) The use of water as the solvent makes a clearing treatment reversible (described later), that is, the use of water as the solvent can bring a biological material having been subjected to a clearing treatment back to a state that it had before the clearing treatment, if necessary. 6) Compared with a case where an organic solvent is used as a main solvent, the use of water as the solvent enhances safety in handling of the clearing reagent.

A "clearing reagent for making a biological material transparent" according to the present invention may be a buffer which can maintain a pH suitable for a biological material to be subjected to a clearing treatment. Further, a "clearing reagent for making a biological material transparent" according to the present invention may have an osmotic pressure adjusted to a degree which further prevents deformation of a biological material to be subjected to a clearing treatment and which allows urea to sufficiently penetrate into the biological material.

Note that, as with the case of urea, the above solvent can also be used for the urea derivative.

(Quantitative Relationship Between Components)

The "clearing reagent for making a biological material transparent" according to the present invention is not particularly limited in terms of an amount of "urea" contained therein, as long as the urea is contained within a range of 1M or more and not more than 8.5M. Note that an upper limit of the amount of urea contained in the clearing reagent is determined by the solubility of urea with respect to a solvent to be used. For example, a clearing reagent with a relatively small amount of urea can perform a required treatment by performing the treatment for a long time, while a clearing reagent with a relatively large amount of urea can perform a required treatment by performing the treatment for a short time, although this depends on the type of the biological material to be subjected to the treatment.

In the case where a "surfactant" is used in a clearing reagent of the present invention, the clearing reagent is not particularly limited in terms of an amount of the surfactant contained therein. Preferably, the surfactant is contained therein at a concentration of 0.025 (w/v) % or more and not more than 5 (w/v) %, more preferably 0.05 (w/v) % or more and not more than 0.5 (w/v) %, particularly preferably 0.05 (w/v) % or more and not more than 0.2 (w/v) %. Note that the unit "(w/v) %" represents a percentage of a weight (w (gram)) of a surfactant used, with respect to a volume (v (milliliter)) of the clearing reagent.

In the case where a "water-soluble macromolecular compound" is used in a clearing reagent of the present invention, the clearing reagent is not particularly limited in terms of an amount of water-soluble macromolecular compound contained therein. Preferably, the water-soluble macromolecular compound is contained therein at a concentration of 2.5 (w/v) % or more and not more than 40 (w/v) %. Further, in view of a balance between a swelling prevention effect for a biological material and a refractive index of the biological material after the clearing treatment, the above concentration is more preferably 5 (w/v) % or more and not more than 25 (w/v) %, further more preferably 10 (w/v) % or more and not more than 20 (w/v) %, particularly preferably 10 (w/v) % or more and not more than 15 (w/v) %. Note that the unit "(w/v) %" represents a percentage of a weight (w (gram)) of the water-soluble macromolecular compound used, with respect to a volume (v (milliliter)) of the clearing reagent.

In the case where the "drying inhibition component" is used in a clearing reagent of the present invention, the clearing reagent is not particularly limited in terms of an amount of the drying inhibition component contained therein. Preferably, the drying inhibition component is contained therein at a concentration of more than 0 (w/v) % and not more than 10 (w/v) %, more preferably 1 (w/v) % or more and not more than 7 (w/v) %, particularly preferably 2.5 (w/v) % or more and not more than 5 (w/v) %. Note that the unit (w/v) % represents a percentage of a weight (w (gram)) of the drying inhibition component used, with respect to a volume (v (milliliter)) of the clearing reagent.

(Subject Biological Material)

A biological material to be subjected to a clearing treatment using a "clearing reagent for making a biological material transparent" of the present invention is not limited to any specific kind. Preferably, the biological material is a material derived from a plant or an animal, more preferably a material derived from an animal such as the one selected from fish, amphibians, reptiles, birds, and mammals, particularly preferably a material derived from a mammal. The mammal is not limited to any specific kind, examples of which encompass: laboratory animals such as mice, rats, rabbits, guinea pigs, and primates except for humans; pet animals such as dogs and cats; farm animals such as cows and horses; and humans.

Alternatively, the biological material may be an individual itself (except for a living human individual). Further alternatively, the biological material may be an organ, a tissue, or a cell taken from an individual of a multicellular organism. A "clearing reagent for making a biological material transparent" of the present invention has excellent ability to make a subject transparent; therefore, even if the biological material is a tissue or an organ (e.g., the whole of or part of a brain) derived from a multicellular animal or an individual itself (e.g., an embryo) of a multicellular animal which is not a human, the biological material can be subjected to a clearing treatment. The "clearing reagent for making a biological material transparent" of the present invention has an extremely large effect of preventing deformation of a biological material, so as to be particularly suitable for making a fragile biological material transparent. Examples of the fragile biological material encompass cells except for plant cells, an embryo, at an early developmental stage, of an animal, a stem cell, a primary cultured cell, a lump (e.g., spheroid, neurosphere, cell aggregates) which is obtained by three-dimensionally growing an established cell in a special culture environment.

Further, the biological material may be either of (i) a material fixed for a telescopic observation and (ii) a non-fixed material. In a case of using a fixed material, the material is preferably immersed in, e.g., a 20 (v/w) % sucrose-PBS solution adequately (e.g., for 24 hours or more) after being subjected to a fixing process. Furthermore, preferably, this material is embedded into an OCT compound and frozen by liquid nitrogen, thawed in PBS, and then fixed again by a 4 (v/w) % PFA (paraformaldehyde)-PBS solution.

Specific examples of the biological material encompass: a biological tissue having a fluorescent chemical substance injected thereto; a biological tissue stained with a fluorescent chemical substance; a biological tissue having a fluorescent protein-expressed cell transplanted thereto; and a biological tissue taken from a genetically-modified animal in which a fluorescent protein is expressed.

(Examples of Particularly Preferable Composition of Clearing Reagent for Biological Material)

The following will describe examples of a particularly preferable composition of a "clearing reagent for making a biological material transparent" according to the present invention. The following clearing reagents are quite suitable for a clearing treatment particularly on an embryo, at an early developmental stage, of a mammal such as a mouse.

Clearing Reagent (1) for Making a Biological Material Transparent:

An aqueous solution obtained by dissolving, in water, (i) urea at a concentration of 3M or more and not more than 5M and (ii) glycerol at a concentration of 25 (w/v) % or more and not more than 35 (w/v) %.

Clearing Reagent (2) for Making a Biological Material Transparent:

An aqueous solution obtained by dissolving, in water, (i) urea at a concentration of 3M or more and not more than 5M, (ii) a nonionic surfactant (e.g., Triton X-100) at a concentration of 0.05 (w/v) % or more and not more than 0.2 (w/v) %, and (iii) glycerol at a concentration of 25 (w/v) % or more and not more than 35 (w/v) %.

Clearing Reagent (3) for Making a Biological Material Transparent:

An aqueous solution obtained by dissolving, in water, (i) urea at a concentration of 3M or more and not more than 5M, (ii) a nonionic surfactant (e.g., Triton X-100) at a concentration of 0.05 (w/v) % or more and not more than 0.2 (w/v) %, (iii) glycerol at a concentration of 25 (w/v) % or more and not more than 35 (w/v) %, and (iv) a water-soluble macromolecular compound (e.g., Ficoll) at a concentration of 2.5 (w/v) % or more and not more than 5 (w/v) %.

Clearing Reagent (4) for Making a Biological Material Transparent:

An aqueous solution obtained by dissolving, in water, (i) urea at a concentration of 3M or more and not more than 5M, (ii) a nonionic surfactant (e.g., Triton X-100) at a concentration of 0.05 (w/v) % or more and not more than 0.2 (w/v) %, and (iii) dimethyl sulfoxide (DMSO) at a concentration of 8 (w/v) % or more and not more than 12 (w/v) %, and (iv) glycerol at a concentration of 25 (w/v) % or more and not more than 35 (w/v) %.

Each of the clearing reagents (1) through (4) for making a biological material transparent contains glycerol at a concentration of preferably 25 (w/v) % or more and not more than 33 (w/v) %, more preferably 27 (w/v) % or more and not more than 33 (w/v) %. Preferably, each of the clearing reagents (1) through (4) for making a biological material transparent contains urea at a concentration of 3.5M or more and not more than 4.5M, more preferably 3.7M or more and not more than 4.3M.

Note that in the case where the urea derivative (or a mixture of urea and the urea derivative) is used instead of urea, the clearing reagents (1) through (4) may be prepared with the urea derivative (or the mixture) at the same concentration as the above-described concentration of urea.

(Preparation of Clearing Reagent for Making Biological Material Transparent)

A method for preparing a "clearing reagent for making a biological material transparent" according to the present invention includes dissolving, in a solvent, (i) "urea and/or a urea derivative", (ii) "glycerol", and (iii) a "surfactant", a "water-soluble macromolecular compound", a "drying inhibition component", and/or the like, each of which is used if necessary. A procedure for dissolving or mixing the components in the solvent is not particularly limited.

(Example of Method for Clearing Treatment Using Clearing Reagent for Making Biological Material Transparent)

A method for a clearing treatment on a biological material with use of a "clearing reagent for making a biological material transparent" according to the present invention includes a step (clearing treatment step) for causing the clearing reagent to permeate into the biological material. More specifically, this step causes the clearing reagent to permeate into the biological material in a container for a clearing treatment.

In the clearing treatment step, whether the clearing reagent or the biological material is stored in the container for the clearing treatment first is not particularly limited. Preferably, the clearing reagent is stored in the container first, and subsequently the biological material is stored therein (i.e., the biological material is put into the clearing reagent).

A processing temperature at which the above clearing treatment step is performed is not particularly limited; preferably, the processing temperature is within a range of 15° C. or more and not more than 45° C. A processing time for which the clearing treatment is performed is not particularly limited; preferably, the processing time is within a range of two hours or more and not more than six months, more preferably 72 hours or more and not more than 21 days. A pressure at which the clearing treatment is performed is not particularly limited.

The container for the clearing treatment which is used in the above clearing treatment step and in which the biological material having been subjected to the clearing treatment is stored may be preserved, e.g., at room temperature or in a low-temperature environment until the container is used in the below-described observation step.

(A Step for Preserving a Sample after a Clearing Treatment)

(Step for Observation of Biological Material Having been Subjected to Clearing Treatment)

On the biological material having been subjected to the clearing treatment, an observation step by, e.g., an optical microscope is subsequently performed. On the biological material to be subjected to the observation step, a visualizing treatment step (e.g., staining or marking) may be performed (i) before the clearing treatment step or (ii) after the clearing treatment step but before the observation step, if necessary.

For example, in a case where the visualizing treatment step involves use of a fluorescent protein, a fluorescent protein gene is transferred into a living biological material before the clearing treatment step so that the fluorescent protein will be expressed therein.

In a case where the visualizing treatment step is (i) injection of a fluorescent chemical substance (which is not a fluorescent protein) into a biological material or (ii) staining of a biological material with a fluorescent chemical substance, the visualizing treatment step is preferably performed before the clearing treatment step. However, such the visualizing treatment step may be performed after the clearing treatment step. Alternatively, the visualizing treatment step may be staining of a biological material with a chemical substance which is not a fluorescent chemical substance.

The observation step can be performed with use of any type of optical microscope. For example, the observation step can be performed by employing a three-dimensional super-resolution microscopy technique (e.g., STED, 3D PALM, FPALM, 3D STORM, or SIM). Preferably, the observation step is performed by employing a multi-photon excitation type (generally, two-photon excitation type) optical microscopy technique.

Note that according to the present invention, it is one of indications of a clearing (treatment) that in a case where a biological material before the clearing treatment and a biological material after the clearing treatment are compared with each other, the biological material after the clearing treatment is more improved in light (particularly, visible light) transmittance than the biological material before the clearing treatment.

(Other Applications)

A clearing treatment using a "clearing reagent for making a biological material transparent" according to the present invention is reversible. As such, a biological material having been subjected to the clearing treatment can be brought back to a state that it had before the clearing treatment, e.g., by immersing the biological material in an equilibrium salt solution so as to remove therefrom the components of the clearing reagent. Here, specific examples of the equilibrium salt solution encompass: equilibrium salt solutions (e.g., PBS and HBSS) which are buffered by phosphate; an equilibrium salt solution (TBS) which is buffered by tris hydrochloride; an artificial cerebrospinal fluid (ACSF); and basal media for cell culturing, such as MEM, DMEM, and Ham's F-12.

The use of the clearing reagent does not cause denaturation or the like of a protein, etc. in the biological material, before and after the clearing treatment, or in a case where, after the clearing treatment, the biological material is brought back to a state that it had before the clearing treatment. Accordingly, antigenicity of the protein, etc. in the biological material is preserved as unchanged. As such, for example, after a biological material is subjected to a clearing treatment and an optical microscopic observation, the biological material can be brought back to a state that it had before the clearing treatment, so as to undergo, e.g., a detailed assay by means of generally-used tissue staining or immunostaining.

In other words, another aspect of the present invention is a method for recovering a biological material which method includes a step of causing an equilibrium salt solution to permeate into a biological material having been made transparent by a clearing treatment by use of the "clearing reagent for making a biological material transparent", in order that the biological material is brought back to a state that the biological material had before the clearing treatment.

(Kit for Clearing Treatment for Making Biological Material Transparent)

A "kit for a clearing treatment for making a biological material transparent" according to the present invention includes the above-described "clearing reagent for making a biological material transparent". The "kit for a clearing treatment for making a biological material transparent" may further include at least one selected from: a "container for a clearing treatment" used in the clearing treatment step; a "biological material holding tool (e.g., tweezers)"; an "equilibrium salt solution" for bringing a biological material having been subjected to a clearing treatment back to a state that it had before the clearing treatment; and an "instruction manual for the kit". Note that, the instruction manual for the kit describes, for example, a procedure for the clearing treatment method, which is described above in the section (Example of Method for Clearing Treatment Using Clearing Reagent for Making Biological Material Transparent).

(System for Clearing Treatment for Making Biological Material Transparent)

A system for a clearing treatment for making a biological material transparent according to the present invention includes: a "clearing reagent for making a biological material transparent" according to the present invention; and the above-described "biological material" which has been isolated. Further, in this system, the clearing reagent has permeated into the biological material so as to make the biological material transparent. That is, a concept of this system for a clearing treatment encompasses, e.g., (i) a treatment system including a biological material which is in a midterm stage of a clearing treatment or (ii) a treatment system including a biological material on which a clearing treatment has been completed.

EXAMPLES

The following will further specifically describe the present invention with reference to Examples, Comparative Examples, etc. below. However, the present invention is not limited to these.

Example 1

Observation of Brain Slices (Step for Perfusion Fixation)

A wild-type (nongenetically-modified) normal C57BL6 male mouse of 6 week-old after birth was used. A peristaltic pump was used to perfuse an ice-cold PBS from the left cardiac ventricle of the mouse, and then to perfuse an ice-cold fixing solution (4% paraformaldehyde-PBS, pH 7.4), so that the mouse was systemically fixed.

(Step for Taking-Out and Fixing of Biological Material)

Subsequently, the cranial bones were removed from the mouse, and the whole of the brain was carefully taken out therefrom. Then, the brain taken out was immersed in an ice-cold fixing solution (4% paraformaldehyde-PBS, pH 7.4) for one night at 4° C. Thereafter, the brain was transferred into a 20% sucrose-PBS solution, and was then gently shaken for 24 hours at 4° C.

Next, after the brain was completely replaced by the 20% sucrose-PBS solution, the brain was embedded into an OCT compound, and was then frozen by liquid nitrogen. Then, the frozen brain was put into PBS, and was thawed at room temperature. The brain thawed was refixed in a 4% paraformaldehyde-PBS for an hour.

(Step for Clearing Treatment and Observation of Biological Material)

Lastly, a coronal-sectioned slice (thickness: 3 mm) including the hippocampus was prepared from the refixed brain. Next, the coronal-sectioned slice was cut along the center line into a right hemisphere slice and a left hemisphere slice. Then, one of the right and left hemisphere slices was immersed in a SCALE-A2 reagent and was shaken at room temperature for 48 hours for a clearing treatment. The other one of the right and left hemisphere slices was immersed in a clearing reagent U for making a biological material transparent and was shaken at room temperature for 48 hours for a clearing treatment. Next, a 1.5 mm-thickness coronal-sectioned slice including the hippocampus was cut out of each of these coronal-sectioned slices. Coronal-sectioned slices thus obtained were used in an observation step.

Note that the SCALE-A2 reagent was an aqueous solution prepared by dissolving, in pure water, 4M urea, 0.1% (w/v) Triton X-100, and 10% (w/v) glycerol. The clearing reagent U was an aqueous solution prepared by dissolving, in pure water, 4M urea, 0.1% (w/v) Triton X-100, and 30% (w/v) glycerol.

In the observation step, a spectrophotometer (product name: U-3310 Spectrophotometer, manufactured by Hitachi, Ltd) was used to measure a transmission spectrum of the 1.5 mm-thickness coronal-sectioned slice with light in a wavelength region of 300 nm to 920 nm.

As a reference example, a coronal-sectioned slice (thickness: 3 mm) including the hippocampus was prepared from a refixed brain. Next, the coronal-sectioned slice was cut along the center line into a right hemisphere slice and a left hemisphere slice. Then, one of the right and left hemisphere slices was immersed in PBS and was shaken at room temperature for 48 hours. Thus prepared was a 1.5 mm-thickness coronal-sectioned slice including the hippocampus.

Figure 1:
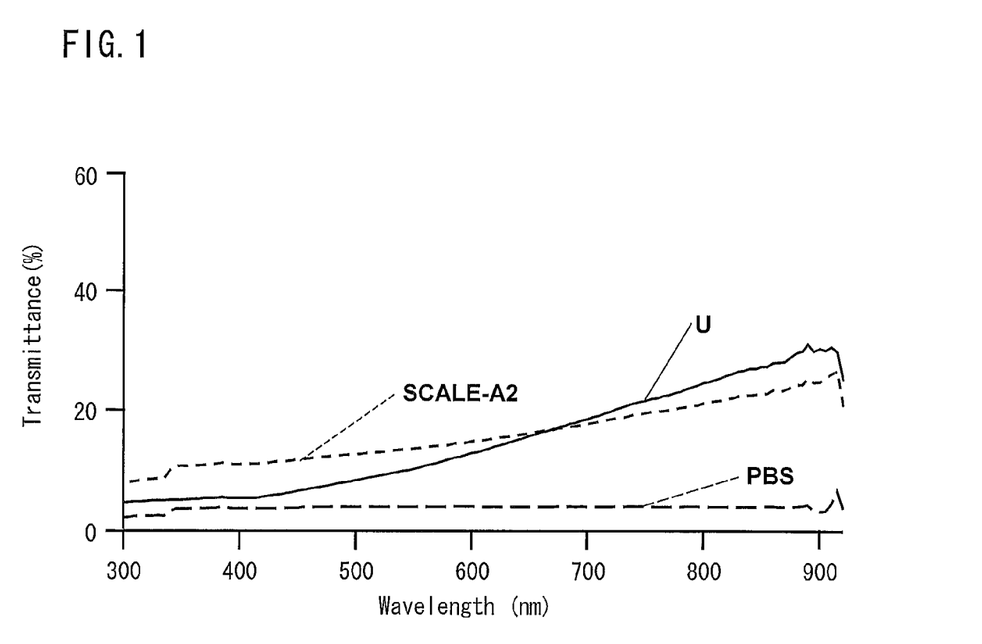
FIG. 1, related to an example of the present invention, is a view showing the result of light transmittance measurement of a mouse brain slice having been subjected to a clearing treatment with clearing a reagent according to the present invention for making a biological material transparent.

The result of the observation is shown in FIG. 1. In FIG. 1, "U" is a result obtained from the treatment with use of the clearing reagent U in the present example, "SCALE-A2" is a result obtained from the treatment with use of the SCALE-A2 reagent, and "PBS" is a result obtained from the treatment with use of the PBS in the reference example. As shown in FIG. 1, it was confirmed that, although varying from wavelength to wavelength, "U" and "SCALE-A2" were each made transparent as compared with the reference example.

Note that, although data is not shown, the SCALE-A2 reagent, the clearing reagent U, PBS, and water have substantially the same transmission spectrum with light in a wavelength region of 300 nm to 920 nm.

Example 2

Clearing Treatment for Making Mouse Embryo Transparent

A Fucci-S-Green (Fucci-S/$G_2$/M)- and Fucci-$G_1$-RED (Fucci-$G_1$)-expressed transgenic mouse embryo at 11.5 days of embryonic life and a Fucci-S-Green (Fucci-S/$G_2$/M)- and Fucci-$G_1$-RED (Fucci-$G_1$)-expressed transgenic mouse embryo at 13.5 days of embryonic life (each obtained by breeding of mice produced by Laboratory for Cell Function Dynamics, Brain Science Institute, RIKEN [reference: Sakaue-Sawano et al., Cell, 132(3): 487-98, 2008.]) were each fixed with 4 (v/w) % PFA-PBS for two days, and then immersed in a 20 (v/w) % sucrose-PBS solution. Thereafter, the embryos were frozen once, and were then thawed. After that, the embryos were fixed again with 4 (v/w) % PFA-PBS for an hour. Each of the transgenic mice was obtained by crossing a line #504 expressing Fucci-S/$G_2$/M and a line #596 expressing Fucci-$G_1$. In the transgenic mouse, a cell in the S/$G_2$/M cell cycle phases emits green fluorescence, and a cell in the $G_1$ cell cycle phase emits red fluorescence. Note that the line #504 and the line #596 are described in the above reference, and are available to a third party.

Subsequently, the embryos were each immersed in a clearing reagent U, which is identical to the clearing reagent U used in Example 1, for 3 months for a clearing treatment.

Next, the embryos were each embedded in agarose gel (concentration: 0.5% (w/v) or less), and observed by being irradiated with predetermined excitation light with use of a confocal fluorescent stereomicroscope (macro zoom LSCM (AZ-C1), manufactured by Nikon Corporation). Note that an objective lens (AZ-Plan Flour, N.A.=0.2, W.D=45 mm) used in image capturing had a magnification of ×2.

Figure 2:
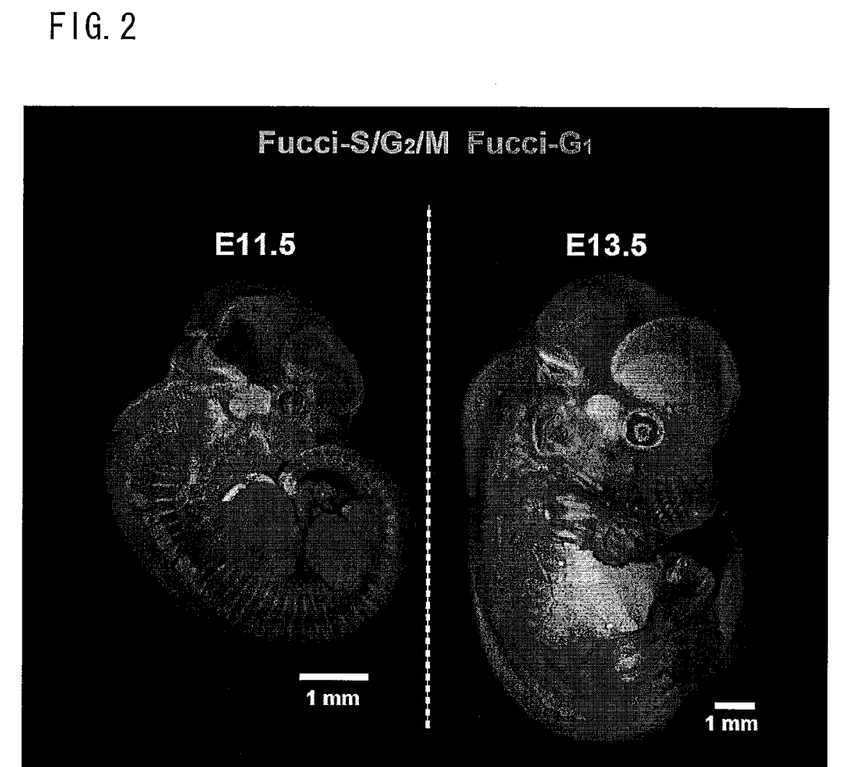
FIG. 2, related to another example of the present invention, is a view showing mouse embryos treated with a clearing reagent according to the present invention for making a biological material transparent.

The result of the observation is shown in FIG. 2. As shown in FIG. 2, by performing the clearing treatment with use of the clearing reagent according to the present example, the whole body of each of the mouse embryos was made transparent outstandingly. This made it possible to detect a cell cycle state of a cell constituting each part of each of the embryos, and thus made it possible to create a three-dimensional cell cycle map of the whole body. In the step for clearing treatment, substantially no change in volume (swelling) of each of the mouse embryos was observed.

Reference Example 1

Recovery of Tissue after Clearing Treatment

From the hippocampi of a GFP transgenic mouse and a YFP transgenic mouse (GFP-M line and YFP-H line, provided by Professor Josh Sanes of Harvard University, U.S.A.), 2.5 mm-thickness slices were prepared. Then, these slices were subjected to a clearing treatment using a SCALE-A2 reagent (see Example 1) for five days so that the slices were made transparent once. Thereafter, the slices were rinsed with PBS three times so that the tissues in the slices were brought back to a non-transparent state. The slices in the non-transparent state were compared with slices having not been subjected to a clearing treatment using a SCALE-A2 reagent, in terms of immunostaining properties.

Note that, as with the case of the reagent U used in Examples 1 and 2, the SCALE-A2 reagent contains urea as an active component for a clearing treatment.

The immunostaining was performed as follows: As a primary antibody, (i) mouse-derived anti-polysialilated neural cell adhesion molecule (PSA-NCAM) monoclonal antibody (Millipore Corporation) that recognizes a polysialic acid of PSA-NCAM existing on a surface of an immature neuronal cell and (ii) rabbit-derived anti-glial fibrillary acidic protein (GFAP) polyclonal antibody (Sigma-Aldrich) that recognizes an intermediate filament GFAP specific to astroglia were used, and were caused to react with their respective target proteins in the slices for 24 hours at 4° C. Thereafter, the slices were rinsed with PBS. Then, the anti-PSA-NCAM monoclonal antibody was caused to react with an Alexa Fluor 546-labeled anti-mouse IgM antibody (Invitrogen, Molecular Probes), which was used as a secondary antibody, at room temperature for three hours; and the GFAP polyclonal antibody was caused to react with an Alexa Fluor 633-labeled anti-rabbit IgG antibody (Invitrogen, Molecular Probes), which was used as a secondary antibody, at room temperature for three hours. In this manner, the slices were immunohistochemically stained. Since fluorescence from these slices did not decayed, triple fluorescent (fluorescence including GFP and YFP) stained images were obtained. The observation was performed with a 20-power objective lens (UplanApo20, Olympus Corporation) with use of an inverted confocal laser microscope (FV500, Olympus Corporation).

Figure 3:
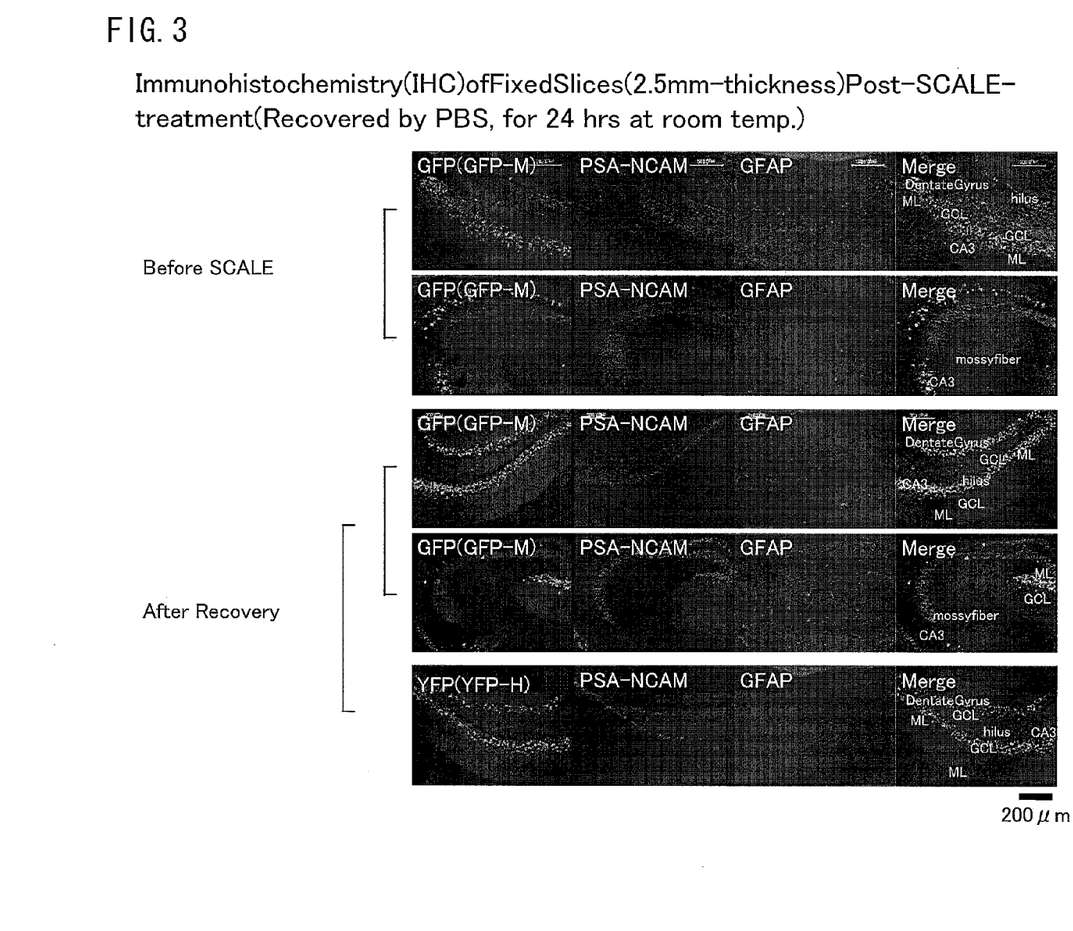
FIG. 3, related to a reference example of the present invention, is a view showing the results of immunostaining on (i) biological materials before a clearing treatment with a clearing reagent for making a biological material transparent, the clearing reagent containing urea as a main component and (ii) biological materials which were, after the clearing treatment, brought back to states that they had before the clearing treatment.

As shown in FIG. 3, both before ("Before SCALE" in FIG. 3 and after ("After Recovery" in FIG. 3) the treatment using SCALE-A2, (i) immature neurons existing in the dentate gyrus of hippocampus and (ii) mossy fibers extending from the immature neurons to the CA3 region were stained with the anti-PSA-NCAM monoclonal antibody with substantially no problem. Similarly, the astroglia was also stained with the anti-GFAP polyclonal antibody without any problem.

Example 3

Clearing Treatment for Making Mouse Embryo Transparent

Embryos at 14.5 days of embryonic life of transgenic mice of the same type as the mice used in Example 2 were immersed in PBS, a clearing reagent U for making a biological material transparent, and a SCALE-A2 reagent, respectively, and were incubated with shaking at room temperature for seven days. Note that the clearing reagent U and the SCALE-A2 reagent have the same compositions as the clearing reagent U and the SCALE-A2 reagent used in Example 1, respectively.

Figure 4:
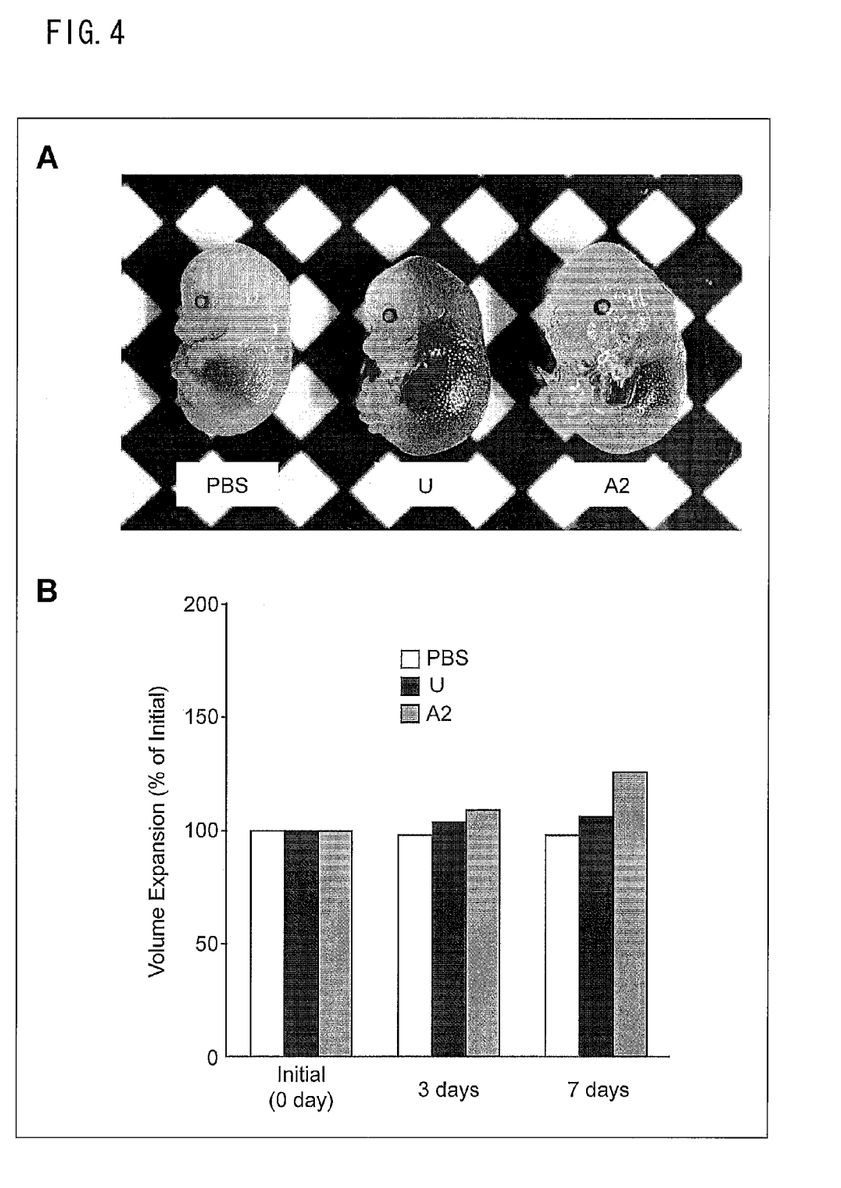
FIG. 4, related to a yet another example of the present invention, is a view showing mouse embryos treated with a clearing reagent according to the present invention for making a biological material transparent.

The result of the incubation is shown in FIG. 4. A of FIG. 4 is a view in which embryos incubated with shaking at room temperature for seven days in the respective solutions are compared with each other. The embryo treated with the PBS was barely made transparent. In the case of the embryo treated with the clearing reagent U, the clearing had progressed, except in the liver, to cause a pattern in the background to be seen through, and there was substantially no change in volume as compared with the case of the embryo treated with the PBS. By contrast, in the case of the embryo treated with the SCALE-A2 reagent, the clearing had slightly progressed, but the embryo swelled as compared with the embryo treated with the PBS and the embryo treated with the clearing reagent U.

B of FIG. 4 is a graph in which a degree to which an embryo swelled is quantified. Measurement of volumes of the embryos was performed as follows. Containers with an identical shape and an identical size were each charged with a certain amount of a solution. The embryos, each serving as a sample, were immersed in the respective solutions, and an increase in fluid volume of each of the solutions was measured, with use of a micropipette, as a volume of the embryo at that point in time. This is indicated as Initial (0 day, measured by immersing the embryo in PBS). Immediately after the initial measurement of the volume, the embryo was immersed in a new PBS, a clearing reagent U, or a SCALE-A2 reagent. Both after three days and after seven days, the solution was replaced with a new solution of the certain amount, and the embryo was immersed in the new solution to measure a volume expansion of the embryo by the above-described method. A value at each point in time was indicated as an average of volume expansions of two embryos used in each solution, and was obtained by calculating, as a relative value, a volume at each point in time relative to 100% of the volume the point in time of Initial (0 day).

A volume of an embryo at the point in time of 7 days after immersion of the embryo in a solution was started was (i) 98.0% of Initial in a case where the solution was the PBS, (ii) 125.3% of Initial in a case where the solution was the SCALE-A2 reagent, and (iii) 106.1% of Initial in a case where the solution was the clearing reagent U. That is, it was confirmed that, a mouse embryo at 14.5 days of embryonic life had a smaller rate of volume change and was made transparent to a greater extent in a case where the mouse embryo had been treated with the clearing reagent U as compared with a case where the mouse embryo had been treated with the SCALE-A2 reagent.

Example 4

Clearing Treatment for Making Mouse Cerebrum Slice Transparent

First, from four wild-type C57BL6/J mice of 8 week-old, 3 mm-thickness slices each including a hippocampus region were prepared with use of an acrylic brain slicer (manufactured by Muromachi Kikai Co., Ltd.). In the preparation, a cerebrum was cut across the both hemispheres at a position located 3 mm closer to the front of the cerebrum than a reference position which was at a backmost part of the center line that divided the cerebrum into right and left. Next, four cerebrum slices, which were thus obtained from the substantially identical positions of the four mice so as to include the hippocampus regions, were each divided substantially equally into right and left along the center line, so that eight slices were obtained.

Figure 5:
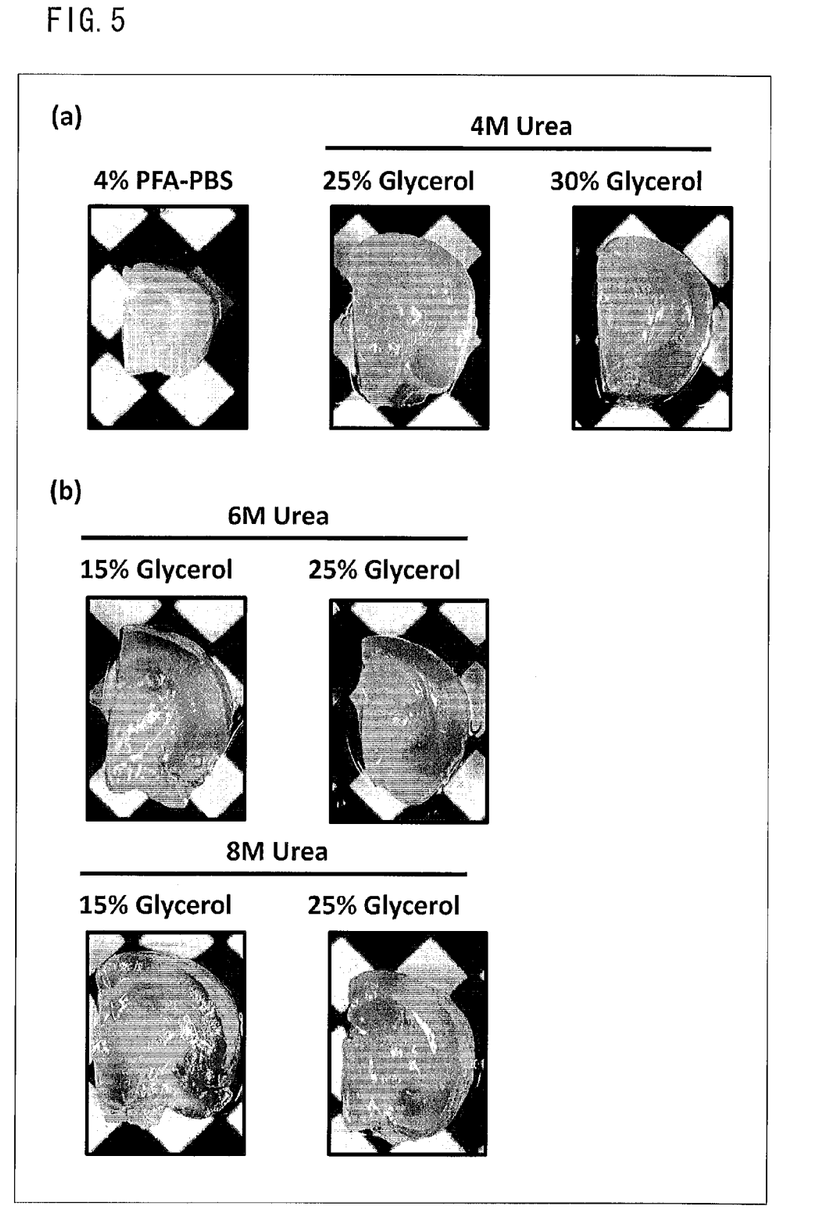
FIG. 5, related to a still yet another example of the present invention, is a view showing mouse cerebrum slices treated with a clearing reagent according to the present invention for making a biological material transparent (see, Example 4 for a description of FIG. 5A and FIG. 5B.

Next, three slices out of the eight slices were immersed in an ice-cold fixing solution, the clearing reagent U, and a clearing reagent U1 for making a biological material transparent, respectively, and were incubated with shaking at room temperature for six days. Note that the three slices had substantially the same size before being subjected to the immersion treatment. The ice-cold fixing solution was a 4% paraformaldehyde (PFA)-PBS. The clearing reagent U1 was an aqueous solution prepared by dissolving, in pure water, 4M urea, 0.1% (w/v) Triton X-100, and 25% (w/v) glycerol. The results are shown in (a) of FIG. 5. Note that, for easy comparison, an image of a right hemisphere slice, which was on the left-hand side among images of right and left hemisphere slices into which a cerebrum had been divided, was inverted so that the both hemispheres face the same direction.

Further, two slices out of the eight slices were respectively immersed in clearing reagents U2 and U3 (reference examples) for making a biological material transparent, and were incubated with shaking at room temperature for six days. Note that the two slices were prepared by dividing a single slice of a cerebrum substantially equally into right and left, and had substantially the same size before being subjected to the immersion treatment. The clearing reagent U2 was an aqueous solution prepared by dissolving, in pure water, 6M urea, 0.1% (w/v) Triton X-100, and 25% (w/v) glycerol. The clearing reagent U3 was an aqueous solution prepared by dissolving, in pure water, 6M urea, 0.1% (w/v) Triton X-100, and 15% (w/v) glycerol. The results are shown in the upper portions of (b) of FIG. 5.

Further, two slices out of the eight slices were respectively immersed in clearing reagents U4 and U5 (reference examples) for making a biological material transparent, and were incubated with shaking at room temperature for six days. Note that these two slices were prepared by dividing a single slice of a cerebrum substantially equally into right and left, and had substantially the same size before being subjected to the immersion treatment. The clearing reagent U4 was an aqueous solution prepared by dissolving, in pure water, 8M urea, 0.1% (w/v) Triton X-100, and 25% (w/v) glycerol. The clearing reagent U5 was an aqueous solution prepared by dissolving, in pure water, 8M urea, 0.1% (w/v) Triton X-100, and 15% (w/v) glycerol. The results are shown in the lower portions of (b) of FIG. 5.

All of the slices immersed in the respective clearing reagents U, U1, U2, and U4 were made transparent. Note that, in the case of a slice, a large amount of water intrudes into the slice in a certain period of time, unlike in the case of a whole body of a mouse embryo covered with skin, in which case water gradually introduces into the body. Accordingly, the slice swells to a greater extent as compared with case of the whole body of the mouse embryo. With these conditions taken into consideration, comparison was made between the clearing reagent U2 and U3 and between the clearing agents U4 and U5. The comparison showed that the clearing reagents U2 and U4 suppressed swelling of a slice more significantly than the clearing reagents U3 and U5, respectively.

The present invention is not limited to the description of the embodiments and examples above, but may be altered by a skilled person within the scope of the claims. An embodiment based on a proper combination of technical means disclosed in different embodiments is encompassed in the technical scope of the present invention.

INDUSTRIAL APPLICABILITY

The present invention provides: a novel clearing reagent for making a biological material transparent which clearing reagent contains, as an active component, a component having a higher bio-affinity; and use thereof.

The invention claimed is:

1. A clearing reagent for making a biological material transparent, consisting essentially of:
   at least one compound selected from the group consisting of urea and urea derivatives at a concentration of 1M or more and not more than 8.5M;
   a surfactant, wherein the surfactant is a nonionic surfactant; and
   glycerol at a concentration of 25 (w/v) % or more and not more than 35 (w/v) %,
   the clearing reagent being a solution,
   wherein the biological material is a cell, an organ taken from an individual of a multicellular organism, a tissue taken from an individual of a multicellular organism, or an individual, which is not a living human individual.

2. The clearing reagent as set forth in claim 1, wherein: urea is contained as the compound.

3. The clearing reagent as set forth in claim 1, wherein the clearing reagent is an aqueous solution.

4. The clearing reagent as set forth in claim 3, further comprising a water-soluble macromolecular compound.

5. The clearing reagent as set forth in claim 4, wherein: the water-soluble macromolecular compound is at least one selected from the group consisting of crosslinked sucrose macromolecular substance, a macromolecular substance obtained by covering colloidal silica with a polyvinyl pyrrolidone film, polyethylene glycol, and polyvinyl pyrrolidone.

6. The clearing reagent as set forth in claim 1, wherein: the nonionic surfactant is at least one selected from the group consisting of a fatty acid surfactant, a higher alcohol surfactant, and an alkylphenol surfactant.

7. The clearing reagent as set forth in claim 1, wherein: the glycerol is contained at a concentration of 27 (w/v) % or more and not more than 33 (w/v) %.

8. The clearing reagent as set forth in claim 1, wherein: the urea is contained at a concentration of 3M or more and not more than 5M, and the surfactant is contained at a concentration of 0.025 w/v % or more and not more than 5 (w/v) %.

9. The clearing reagent as set forth in claim 1, wherein: the clearing reagent makes transparent (i) a tissue or an organ derived from a multicellular animal or (ii) a multicellular animal which is not a human.

10. A system for a clearing treatment for making a biological material transparent, comprising:
    a clearing reagent as set forth in claim 1; and
    a biological material which has been isolated,
    the clearing reagent having permeated into the biological material in order to make the biological material transparent,
    wherein the biological material is a cell, an organ taken from an individual of a multicellular organism, a tissue taken from an individual of a multicellular organism, or an individual which is not a living human individual.

11. A method for making a biological material transparent, comprising the step of:
    causing a clearing reagent as set forth in claim 1 to permeate into a biological material which has been isolated by storing the clearing reagent for making a biological material transparent and the biological material in a container, in order that the biological material is made transparent,
    wherein the biological material is a cell, an organ taken from an individual of a multicellular organism, a tissue taken from an individual of a multicellular organism, or an individual which is not a living human individual.

12. A kit for a clearing treatment for making a biological material transparent, comprising:
    a clearing reagent as set forth in claim 1,
    wherein biological material is a cell, an organ taken from an individual of a multicellular organism, a tissue taken from an individual of a multicellular organism, or an individual which is not a living human individual.

13. A clearing reagent for making a biological material transparent, comprising:
    at least one compound selected from the group consisting of urea and urea derivatives at a concentration of 3M or more and not more than 5M;
    a surfactant, wherein the surfactant is a nonionic surfactant, wherein the surfactant is contained at a concentration of 0.025 (w/v)% or more and not more than 5 (w/v)%; and
    glycerol at a concentration of 25 (w/v)% or more and not more than 35 (w/v)%,
    the clearing reagent being a solution,
    wherein the biological material is a cell, an organ taken from an individual of a multicellular organism, a tissue taken from an individual of a multicellular organism, or an individual which is not a living human individual.

14. The clearing reagent as set fort in claim 13, wherein: urea is contained as the compound.

15. The clearing reagent as set forth in claim 13, wherein the clearing reagent is an aqueous solution.

16. The clearing reagent as set forth in claim 15, further comprising a water-soluble macromolecular compound.

17. The clearing reagent as set forth in claim 16, wherein: the water-soluble macromolecular compound is at least one selected from the group consisting of crosslinked sucrose macromolecular substance, a macromolecular substance obtained by covering colloidal silica with a polyvinyl pyrrolidone film, polyethylene glycol, and polyvinyl pyrrolidone.

18. The clearing reagent as set forth in claim 13, wherein: the nonionic surfactant is at least one selected from the group consisting of a fatty acid surfactant, a higher alcohol surfactant, and an alkylphenol surfactant.

19. The clearing reagent as set forth in claim 13, wherein: the glycerol is contained at a concentration of 27 (w/v)% or more and not more than 33 (w/v)%.

* * * * *